United States Patent [19]
Righetti

[11] Patent Number: 5,834,272
[45] Date of Patent: Nov. 10, 1998

[54] IMMOBILIZED ENZYME REACTOR

[76] Inventor: Pier Giorgio Righetti, Via Archimede 114, Milano, Italy

[21] Appl. No.: 875,294

[22] PCT Filed: Jan. 22, 1996

[86] PCT No.: PCT/EP96/00242

§ 371 Date: Jul. 23, 1997

§ 102(e) Date: Jul. 23, 1997

[87] PCT Pub. No.: WO96/23056

PCT Pub. Date: Aug. 1, 1996

[30] Foreign Application Priority Data

Jan. 24, 1995 [IT] Italy ................................. MI95A0113

[51] Int. Cl.$^6$ .............................. C12N 11/00; C12M 3/00
[52] U.S. Cl. ...................... 435/174; 435/183; 435/285.2; 435/289.1; 435/814
[58] Field of Search .............................. 435/283.1, 285.2, 435/289.1, 814, 174, 183

[56] References Cited

U.S. PATENT DOCUMENTS 5,082,548  1/1992  Faupel et al. ........................ 204/299 R

FOREIGN PATENT DOCUMENTS 0 287 513  10/1988  European Pat. Off. ....... G01N 27/26

*Primary Examiner*—David A. Redding
*Attorney, Agent, or Firm*—Young & Thompson

[57] ABSTRACT

A novel method for immobilizing enzymes, while still keeping them in solution (thus under conditions of homogeneous catalysis), is reported. It consists in blocking enzymes in between two isoelectric membranes, having isoelectric points (pI) on either side of the pI of the enzyme to be "trapped". The reactor consists on a multichamber electrolyzer, in which the electric field is coupled to a hydraulic flow for continuously recycling the enzyme inside and outside the electric field to reservoirs acting as both heat exchangers and as feeders for injecting (or collecting) substrates, cofactors and other reagents. The pH of optimum activity is maintained by co-immobilizing the buffers within the enzyme reaction chamber. This is achieved by selecting appropriate amphoteric buffers, having a pI value comprised between the pI of the two membranes keeping the enzyme isoelectric and possessing a reasonable buffering power at their respective pIs.

10 Claims, 7 Drawing Sheets

IMMOBILIZED ENZYME REACTOR

FIELD OF THE INVENTION

The present invention refers to a process for enzyme immobilization, consisting in trapping said enzymes, while still in solution, between two isoelectric membranes encompassing the isoelectric point (pI) of the enzyme in the reactor. The invention refers also to an enzyme reactor comprising said immobilized enzymes. The reaction chamber of the enzyme reactor consists of a multicompartment electrolyzer, assembled with a set of isoelectric membranes (having pI values increasing monotonically from anode to cathode) and the reaction is preferably (but not exclusively) carried out under the influence of an electric field. In case of charged reactants (and/or products), said substances can be carried electrophoretically into the reaction chamber and/or transported out by the electric field. Also valuable cofactors (e.g., $NAD^+$, NADH) can be moved in and out of the reaction chamber electrophoretically, regenerated outside and fed back into the enzyme reactor. In this way, instead of stoichiometric amounts, only catalytic amounts of coenzymes are required. The present invention refers also to a method for decreasing the water activity in the reaction chamber, thus stabilizing the trapped enzymes. Since catalysis occurs under focusing conditions, with concomitant evacuation of all buffering ions from the reaction chamber, this would quickly lead to enzyme inactivation. The enzyme is kept fully active by the following means: (a) "co-immobilization" of buffers in the enzyme chamber. This is achieved by using amphoteric buffers, with pI values encompassed by the pI values of the two flanking (at anodic and cathodic side, respectively) membranes. A series of such buffers exist covering the pH 3–10 scale;

(b) by addition of polyols (e.g., ethylene glycol, glycerol, erythritol, xylitol, sorbitol) or polymers (e.g., dextrans, polyethylene glycol) or carbohydrates (e.g., sucrose, lactose) to the reaction chambers. Comprised in the present invention are also different means for bringing uncharged substrates electrophoretically into the reaction chamber. Examples of such means are: (a) charging neutral sugars by forming charged complexes with borate; (b) inserting neutral substrates into negatively (e.g., sodium dodecyl sulphate) or positively (e.g., cetyl-trymethyl ammonium bromide) charged micelles. The present invention refers also to the preparation of novel isoelectric membranes by using highly stable acrylamido monomers (in general N-mono- and di-substituted compounds, such as dimethyl acrylamide and N-acryloyl amino ethoxy ethanol), thus allowing stable operation for prolonged period of time, due to their high resistance to alkaline hydrolysis. Still a further object of the present invention is also the possibility of forming highly porous isoelectric membranes (e.g., by the process of lateral aggregation during polymerization) so as to allow unhindered migration in and out of the reaction chamber of macromolecular substrates (e.g., proteins, nucleic acids, lipo- and poly-saccharides). In the present invention, the multicompartment electrolyzer, constituting the reaction chamber, comprises in general an electric field coupled to a hydraulic flow, for recycling enzymes and reactants in and out of the electric field to, e.g., a heat sink or to suitable chromatographic columns, for harvesting valuable reaction products, or to additional reaction chambers for, e.g., regenerating valuable cofactors via secondary enzymatic or chemical reactions. The present invention refers also the use of cascade reactors, where two or more enzymes are coupled serially (e.g. in the same chamber or in adjacent chambers, trapped in between suitable isoelectric membranes), for transforming different substrates (or for performing different modifications on the same substrate) in serial reactions.

BACKGROUND OF THE INVENTION

In the seventies, the field of enzymology received a new impulse due to the introduction of immobilized enzyme reactors (Messing, R. A., Immobilized Enzymes for Industrial Reactors. Academic Press, New York, 1975; Salmona, M., Saronio, C. and Garattini, S., Insolubilized Enzymes, Raven Press, New York, 1974). Among the number of reasons to immobilize enzymes, the most common was simply to facilitate recovery of the enzyme or separation of the product from the catalyst. Such reactors consisted basically of activated enzymes grafted onto a hydrophilic polymeric support, generally in the form of beads. The substrate feed would thus be pumped into the reactor, where it would be converted enzymatically into the desired product, and then flow out leaving behind the catalyst (the enzyme). Soon several variants of this basic methodology were described: enzymes were insolubilized on macroporous cellulose (Kennedy, J. F., in: Salmona, M., Saronio, C. and Garattini, S., eds., Insolubilized Enzymes, Raven Press, New York, 1974, pp. 29–49), on woven fibers during wet spinning (Marconi, W., Gulinelli, S. and Morisi, F., in: Salmona, M., Saronio, C. and Garattini, S., eds., Insolubilized Enzymes, Raven Press, New York, 1974, pp. 51–63), on artificial, porous membranes (e.g., collodion) (Bogulaski, R. C., Bleadel, W. J. and Kissel, T. R., in: Salmona, M., Saronio, C. and Garattini, S., eds., Insolubilized Enzymes, Raven Press, New York, 1974, 87–103), or immobilized by trapping into microcapsules (Chang, T. M. S., in: Salmona, M., Saronio, C. and Garattini, S., eds., Insolubilized Enzymes, Raven Press, New York, 1974, pp. 15–27). Immobilization has also been described onto porous glass beads of controlled porosity (Filbert, A. M., in: Messing, R. A., ed., Immobilized Enzymes for Industrial Reactors. Academic Press, New York, 1975, pp. 39–59) and onto hollow fiber devices (Neetall, H. H., in: Messing, R. A., ed., Immobilized Enzymes for Industrial Reactors. Academic Press, New York, 1975, pp. 99–102). A variety of reactions have also been described for activating polymeric material (the preferred polymers being in general cellulose, agarose and polyacrylamide gels) for subsequent reaction on surface groups of proteins for covalent bonding (cf. Johnson, J. C., Industrial Enzymes, Noyes Data Corp., Park Ridge, 1977, pp. 74–103). Due to the fact that heat and mass transfer processes were less than optimal in heterogeneous catalysis in packed beds, fluidized-beds enzyme reactors were soon proposed (Allen, B. R., Coughlin, R. W. and Charles, M., 1979, Ann. N.Y. Acad. Sci. 326, 105–117), in which catalyst particles were suspended and agitated by an upward flow of liquid through the beds, by using a tapered column, so as to allow a more gradual bed expansion. Since, however, insolubilized enzymes exhibited often much lower reaction rates and different $K_m$ values, attempts were made at producing continuous reactors in which enzymes were kept in solution (i.e. in a homogeneous phase) rather than in a heterogeneous phase. Membrane reactors were thus developed (Wandrey, C., 1979, Ann. N. Y. Acad. Sci. 326, 87–95.; Kim, T. J., Lee, Y. D. and Kim, H. S., 1992, Ann. N.Y. Acad. Sci. 672, 552–557) in which the enzymes were trapped in a reaction chamber by an ultrafiltration membrane (2 to 15 nm average pore diameter), forced to recycle via a loop and mix with substrates by means of a dosing pump. Products (and unconverted substrates) left the reactor through an enforced flow across the ultrafiltration membrane. The advantage of such a technique is that, by being kept in solution, the activity per unit of weight of protein may reach the value of the free native enzyme. Another advantage of such a system is the quick removal of reaction products which might inhibit the enzyme by a feed-back mechanism. In order to solve the problem of a rapid removal of reaction products, enzyme catalysis in a two-phase system was also proposed (Chang, H. N. , Lee, Y. H. and Lee, C. Y., 1992, Ann. N.Y. Acad. Sci. 672, 643–648).

All systems described above suffer from some type of drawbacks E.g., in the case of immobilization by covalent attachment onto polymeric materials (in the form of beads, sheets, filaments), the reaction constants ($K_m$ and $K_i$), pH of optimum of activity and reaction rate could be quite different from the soluble enzyme, in general with a poorer performance of the insolubilized enzyme. Thus, continuous reactors in which enzymes are kept in solution appear to be a valuable alternative. The systems which come closest to realizing this concept are membrane reactors, in which ultrafiltration cells are used to trap the enzyme against a physical barrier, based on a sieving mechanism. By applying pressure to these cells, the membrane itself is used to separate the product stream from the reaction solution containing the enzyme. Yet, even these latter systems are not immune from severe drawbacks. One of the major problems of such systems is that, upon activation of the ultrafiltration process, the flux can be severely hampered by the rapid formation of a concentration polarization layer of enzyme molecules or proteinaceous material building up against the membrane. In addition, the localized enzyme in the polarization layer cannot be utilized to its full reactivity because of the short contact time of the substrate with the enzyme. Additionally, most membranes bear some type of charge and/or are hydrophobic, thus resulting on protein adsorption onto the membrane itself, which ultimately leads to a poor performance of the reactor.

Multicompartment electrolyzers with isoelectric membranes were recently introduced by us (Righetti, P. G., Wenisch, E. and Faupel, M., 1989, J. Chromatogr. 475 293–309; Righetti, P. G., Wenisch, E., Jungbauer, A., Katinger, H. and Faupel. M., 1990, J. Chromatogr. 500, 681–696; Righetti, P. G., Faupel, M. and Wenisch, E., 1992, In: Advances in Electrophoresis, Vol. 5, Chrambach, A., Dunn, M. J. and Radola, B. J., eds., VCH, Weinheim, pp. 159–200) for processing large volumes and amounts of proteins to homogeneity. This purification procedure, based on isoelectric focusing, progresses under recycling conditions, by keeping the protein macroions in a reservoir and continuously passing them in the electric field across a multicompartment electrolyzer equipped with zwitterionic membranes. In this system, the protein is always kept in a liquid vein (thus it is not lost by adsorption onto surfaces, as customary in chromatographic procedures) and it is trapped into a chamber delimited by two membranes having pIs encompassing the pI value of the protein being purified. Thus, by a continuous titration process, all other impurities, either non isoelectric or having different pI values, are forced to leave the chamber, in which the protein of interest will ultimately be present as the sole species, characterized by being isoelectric and isoionic as well (note that the isoelectric and isoionic points of a protein can differ to some extent in the presence of counterions in the solvent). This purification procedure was successfully applied to a number of proteins, such as recombinant human growth hormone (Ettori, C., Righetti, P. G., Chiesa, C., Frigerio, F., Galli, G. and Grandi, G., 1992, J. Biotechnol. 25, 307–318), the epidermal growth factor receptor (Weber, W., Wenisch, E., Gunther, N., Marnitz, U., Betzel, C. and Righetti, P. G., 1994, J. Chromatogr. A 679, 181–189), recombinant superoxide dismutase (Wenisch, E., Vorauer, K., Jungbauer, A., Katinger, H. and Righetti, P. G. ,1994, Electrophoresis 15, 647–653) and glucoamylase (Wenisch, E. , Schneider, P., Hansen, S. A., Rezzonico, R. and Righetti, P. G., 1993, J. Biochem. Biophys. Methods 27, 199–213).

In the original patent describing this process (Faupel, D. M. and Righetti, P. G., U.S. Pat. No. 4,971,670, Nov. 20, 1990) such isoelectric focusing process in presence of buffering, isoelectric membranes, was developed solely and exclusively for separation and purification of proteins and peptides, i.e. for removing contaminants (including other macroions and salts) from the protein of interest. Isoelectric membranes have also been covered by another patent (Martin, A. J. P. and Hampson, F., U.S. Pat. No. 4,243,507, 1981), but in this last process solely for the purpose of suppressing electrosmotic flow generated by fixed or adsorbed charges on the electrophoretic cell. It is the basis of this patent that multicompartment electrolyzers can indeed be used as enzyme reactors, under conditions of continuous homogeneous catalysis, since the enzyme can be kept in solution, but trapped in between two isoelectric membranes, and the reaction products (when naturally charged or induced to bear a charge) continuously removed electrophoretically into adjacent chambers. Additionally, also cofactors could be collected, regenerated and recycled into the enzyme chamber.

There are fundamental differences between the present invention and the one described in the patent of Faupel and Righetti (U.S. Pat. No. 4,971,670, Nov. 20, 1990). First of all, in the above patent, one has to use isoelectric membranes in a very narrow pH interval (even as narrow as 0.01 pI units or, in extreme cases, with $\Delta pI=0$) so as to eliminate protein impurities having very close pI values. On the contrary, in the present case, one has to use generally a relatively high value of $\Delta pI$, so as to maintain, in the "isoelectric trap", both the enzyme and the buffer ensuring an optimum of pH activity. In other words, the enzyme does not necessarily have to operate under isoelectric conditions, whereas the only operative mode, in the case of protein purification, is that all the components to be purified and recovered are, for all practical purposes, isoelectric. Secondly, whereas in the multicompartment electrolyzer, as used for protein purification, the protein is fully desalted, and thus is recovered isoionic, in the present enzyme reactors the enzyme cannot and should not be desalted, as this would lead to loss of enzyme activity. In fact, special precautions are adopted so as to maintain, in the enzyme reaction chamber, both the catalytic macromolecule and the buffers controlling the solution pH and ensuring an optimum of enzyme activity as well as its stability. All these conditions were not contemplated and could not be implemented according to the use suggested in U.S. Pat. No. 4,971,670.

BRIEF DESCRIPTION OF THE DRAWINGS

LEGENDS

FIG. 1

Exploded view of the multicompartment electrolyser. A: rectangular supporting legs; B: Pt electrode; C: thin terminal flow chamber; D: rubber rings for supporting the membrane; E: isoelectric Immobiline membrane cast onto the glass-fiber filter; F: O-ring; G: one of the sample flow chamber; H: four treated metal rods for assembling the apparatus; I: nuts for fastening the metal bolds.

FIG. 2

Scheme of the assembly of the multicompartment electrolyzer. The pI values and the position of the isoelectric membranes are indicated by vertical arrows. The horizontal arrows indicate electrophoretic transport of reaction product and NAD$^+$. Chamber numbering goes from left to right, chamber No. 1 being the anodic compartment (pH 3.0). The external addition of substrate and NADH to the enzyme chamber (No. 3) is indicated by a slanted arrow. DHCA: dehydrocholic acid.

FIG. 3

Scheme of the enzymatic reaction of β-hydroxysteroid dehydrogenase (3β-HSDH). The substrate and reduced cofactor are on the left side; the product and oxidized cofactor on the right side.

FIG. 4

Kinetics of loss of enzyme activity upon different storage conditions. Ctrl.: control, enzyme kept in distilled water. One hundred mM His: enzyme dissolved in isoelectric histidine. One hundred mM His, NADH: enzyme dissolved in isoelectric histidine in presence of the cofactor.

FIG. 5

Capillary zone electrophoretic analysis of converted cofactor (NAD$^+$). CZE run in a 40 cm long, 50 μm I.D. capillary, filled with 75 mM MOPS-Na buffer, pH 7.0. Sample injection by hydrostatic pressure for 5 s. Run: 20 kV; detection at 254 nm. I.S.: internal standard (0.1 mM adenosine 5'-diphospho-ribose) added for quantitation purposes.

FIG. 6

Colorimetric determination of ammonia production in the urease electrolyzer, under a wide range of substrate concentrations, from 5 to 30 mM. Note that the initial rate is linear up to 200 min, as opposed to only a few min in batch reactors.

FIG. 7

Measurement of residual urease activity in a batch (broken line) as opposed to a multicompartment (solid line) reactor. At a time point (200 min) at which 90% activity has been lost in a batch-type operation, only 2% enzyme activity has been lost in the electrolyzer set-up.

DESCRIPTION OF THE INVENTION

Figure 1:
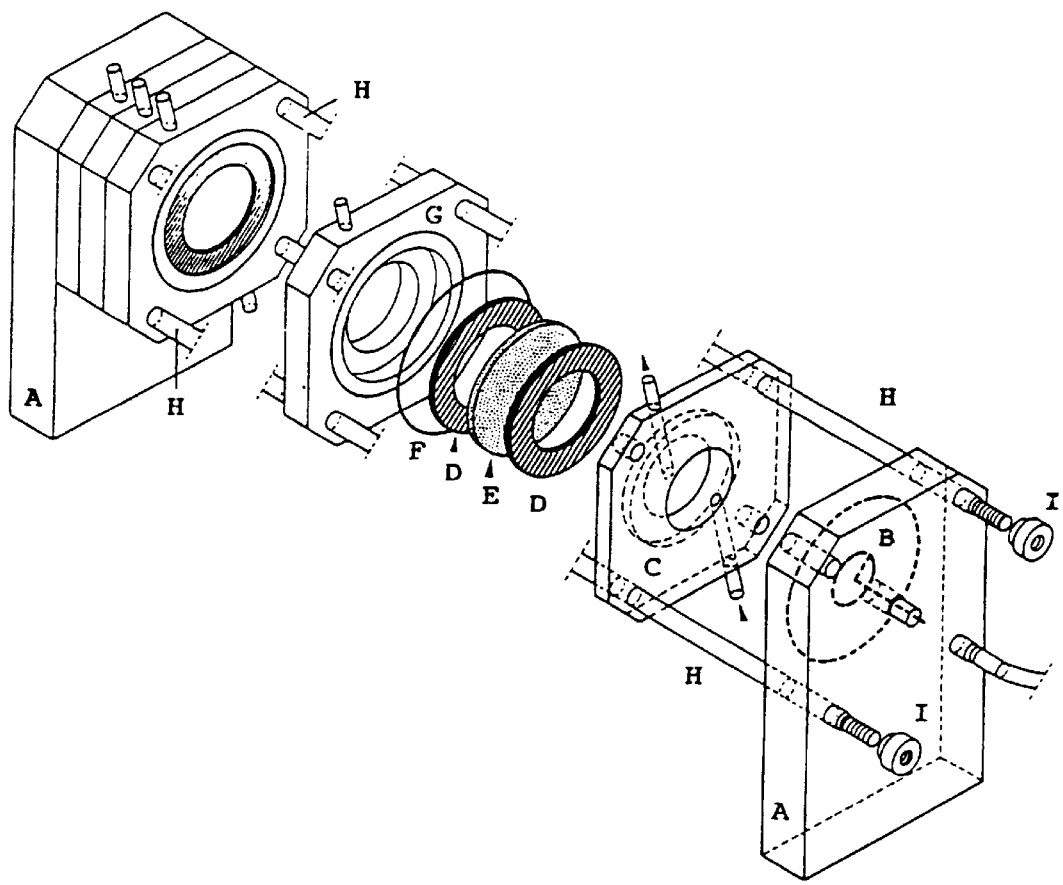

The present invention proposes a novel concept for immobilizing enzymes, while keeping them in solution: "isoelectric traps". A typical apparatus used as enzyme reactor is shown in FIG. 1: it is essentially a multicompartment electrolyzer, as used for protein purification under focusing conditions. It consists of a stack of chambers G sandwiched between an anodic and cathodic reservoir. In FIG. 1, a stack of three chambers already assembled is visible to the left, followed by a central compartment and a terminal chamber C for connection to the other electrode B. All flow chambers are provided with inlet and outlet for sample and electrolyte recycling, an O-ring F for ensuring flow-tight connections and four holes for threading four long metal rods H which can be tightened by manually adjusted butterfly nuts I for assembling the apparatus. The isoelectric, pH-controlling membranes E are housed in the central depression between two 1-cm-wide rings of rubber D. After assembling and tightening the apparatus, each compartment is flow tight, so that no net bulk liquid flow ensues. The Pt electrodes are housed in two rectangular Perspex mountings, which B also act as legs A on which the electrolyzer stands. In general, a free acid is used as anolyte, a free base as catholyte and the enzyme is loaded into a chamber flanked by two zwitterionic, highly buffering membranes which keep it isoelectric all the time, by a continuous titration process. Thus the enzyme is ipso facto immobilized and cannot leave the "isoelectric trap", while charged reactants and products can be transported electrophoretically in and out of the enzyme chamber. The enzyme solution is continuously recycled in and out of the electric field into a reservoir, which is used as both, a heat sink for dissipating the joule heat and thermostatting the enzyme at the desired reacting temperature and as a feeder for (charged or uncharged) substrates, cofactors and stabilizers [such as zwitterionic buffers, polyols (e.g., ethylene glycol, glycerol, erythritol, xylitol, sorbitol), polymers (e.g., dextrans, polyethylene glycol), carbohydrates (e.g., sucrose, lactose)].

Figure 2:
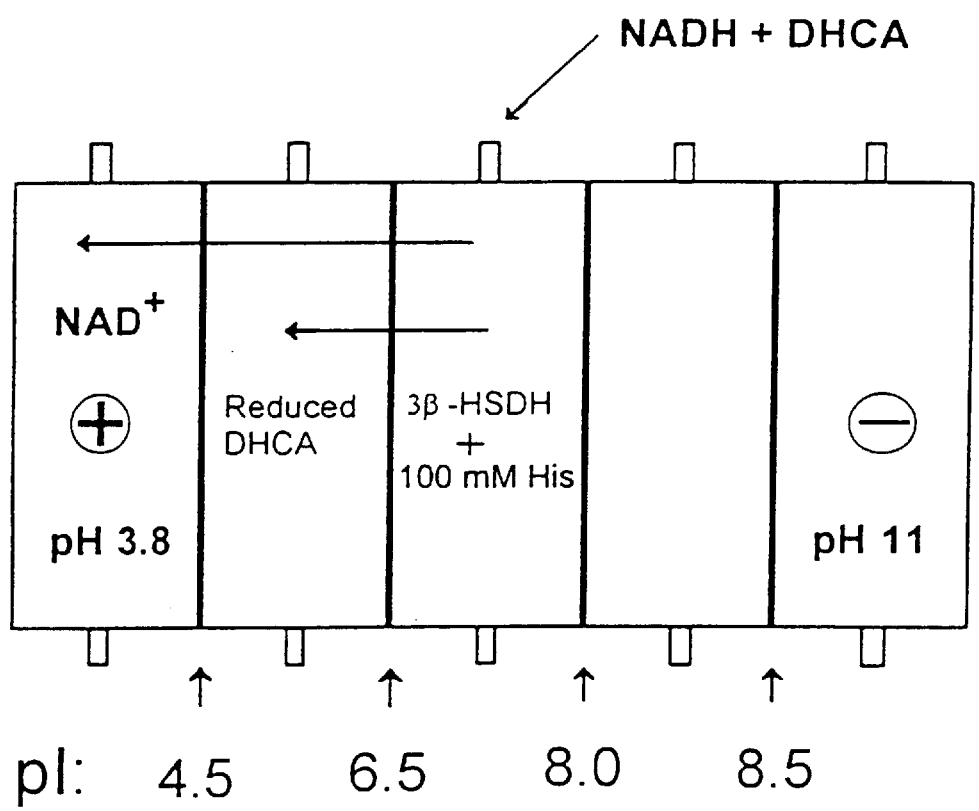
Figure 3:
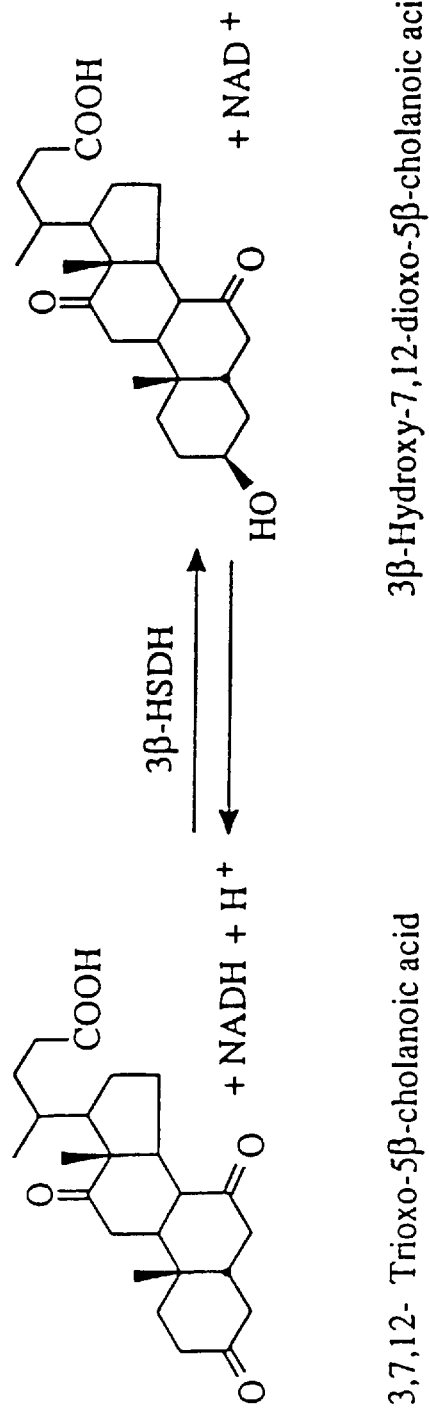

FIG. 2 shows the experimental set-up of the "immobilized enzyme reactor" assembled under an electric field in the apparatus described in FIG. 1. The enzyme tested (β-hydroxysteroid dehydrogenase, 3β-HSDH) is "immobilized" in solution by being kept isoelectric between two membranes, having pIs 8.0 (at the cathodic side) and 6.5 (at the anodic side) (the pI of 3β-HSDH being 6.8). The reactants (dehydrocholic acid, the substrate, and NADH, the cofactor) are slowly pumped into chamber 3. The reaction product (3β-hydroxy-7,12-dioxo-5β-cholanoic acid, a compound of pharmaceutical interest) and the excess, unconverted substrate migrate into chamber 2, where they are arrested by protonation and where the produced bile acid is collected by precipitation (with some unreacted substrate co-precipitating). The oxidized cofactor (NAD$^+$) migrates through chamber 2 and is finally collected into chamber 1, where it ceases migrating due to attainment of isoelectric conditions (the pI of NAD$^+$ being 3.0). The overall reaction scheme is shown in FIG. 3. The experimental conditions in FIG. 2 are as follows: the anodic chamber contains dilute acetic acid, to pH 3, whereas the cathodic chamber contains 1 mM NaOH, pH 11. The four isoelectric membranes are made with the following pI values: 8.50, 8.0, 6.5 and 4.5. All membranes were made to contain 8% T, 4% C matrix, produced with the novel N-acryloyl amino ethoxy ethanol monomer, since it is much more resistant to hydrolysis upon prolonged operation and containing appropriate amounts of Immobilines (acrylamido acids and bases) so as to produce the desired pI values and the required buffering power. The membranes have a diameter of 4.7 cm and a thickness of ca. 1 mm and, upon casting, are supported by glass fiber filters. Their composition has been calculated with the aid of dedicated computer programs (Giaffreda, E., Tonani, C. and Righetti, P. G., 1993, J. Chromatogr. 630, 313–327) so as to provide an average buffering power of 5 milli equivalents L$^{-1}$ pH$^{-1}$. After washing and equilibrating the membranes in 20% (v/v) glycerol, the multicompartment apparatus is assembled and the 3β-HSDH amount (3 mL of 2 mg/mL, corresponding to 14.9 U, dissolved into 14 mL of 100 mM His) loaded into chamber 3. Chambers 4 and 2 are filled with 30 mL of water. The run is started at 5 mA constant and then a total of 18 mL of a solution obtained by mixing 8 mL of 50 mM dehydrocholic acid in 100 mM His and 10 mL of 50 mM NADH in 100 mM His slowly added (100 μL/min) over a period of 3 hours.

Figure 4:
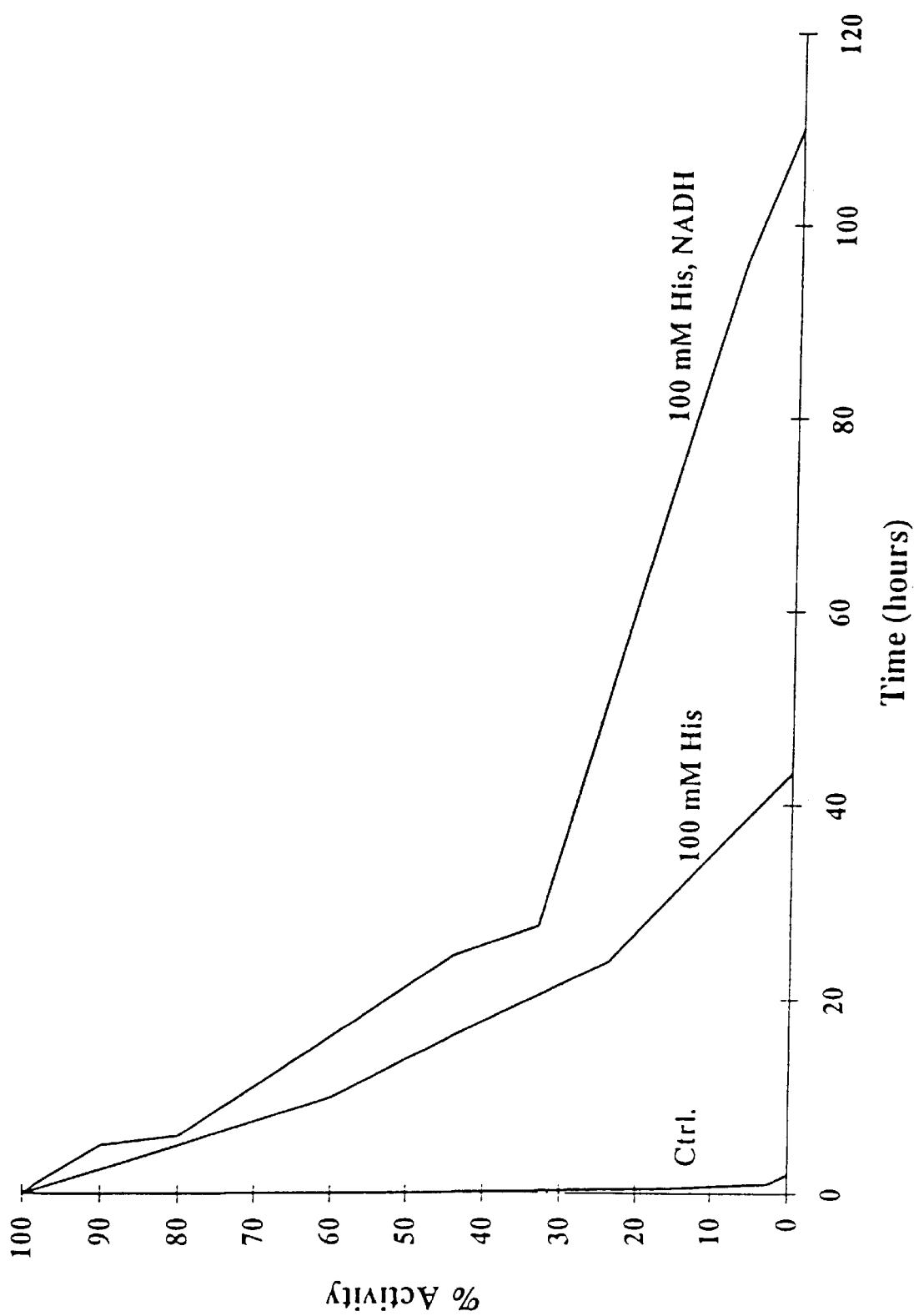

Since, in principle, in chamber 3, the enzyme solution would quickly be deprived of buffering ions (which will keep migrating out of the chamber in the electric field), we have checked the stability of 3β-HSDH under these experimental conditions. As shown in FIG. 4, the enzyme, if kept in plain distilled water, loses very rapidly (within 15 min) 50% of the initial activity and becomes completely inactive in only 2 hrs. Stabilization can be achieved in presence of 100 mM His: as shown in FIG. 4, 50% loss of enzyme activity now occurs in 14 hrs, instead of 15 min. It should be noted that, when the enzyme reaction takes place in the multicompartment apparatus depicted in FIG. 1 (in chamber 3, delimited by two membranes having pIs of 8.0 and 6.5), not only the enzyme is kept isoelectric and prevented from migrating out of this chamber, but also His, when added as a buffering ion, is kept isoelectric (pI of His=7.47) and thus is unable to leave the reaction chamber. Thus, enzyme reactions can occur under fully buffered conditions, provided a zwitterionic buffer, of suitable pI value, is added to the reaction chamber. Further enzyme stabilization can be obtained in presence of the cofactor (NADH). As shown in FIG. 4, when the enzyme is kept in presence of both 100 mM His and NADH (the standard amount added for enzymatic reaction), the enzyme now loses 50% of its activity in 22 hrs. Thus, the enzyme reaction in the electric field can be kept operating for several days (after 3 days of operation, 20% activity is still present and the enzyme is extinguished at ca. 110 hrs; note that the same fate occurs to the enzyme if kept in solution outside the electric field).

At steady-state, the reactor is operated at a constant amperage of 5 mA while feeding (at a rate of 100 $\mu$L/min) a total of 18 mL of a solution of 22 mM dehydrocholic acid and 27 mM NADH to chamber 3 [containing a total volume of 17 mL of 3$\beta$-HSDH (14.9 U) in 100 mM His]. Since 18 mL of substrate/cofactor solution have been added at the end to 17 mL of enzyme, the total final volume in the enzyme reactor is 35 mL. As the reaction progresses, the bile acid product is electrophoretically transported into chamber 2, where it is collected by two mechanism: its migration ceases by protonation of the carboxyl group, which in turn induces its precipitation. When the collected precipitate is analyzed by TLC, it is seen to be composed by 80–90% 3$\beta$-hydroxy-7,12-dioxo-5$\beta$-cholanoic acid (the reaction product) contaminated by 20–10% dehydrocholic acid (the substrate), which probably co-precipitates with the main product. It should be noted that, under static conditions (enzyme reaction occurring outside the electric field), the conversion efficiency is lower (70:30), due to reaction equilibrium. Thus, the reaction efficiency of the "insolubilized enzyme" is even better than that of the free enzyme. Additionally, the recovery of the bile acid product in chamber 2 has been quantitative.

Figure 5:
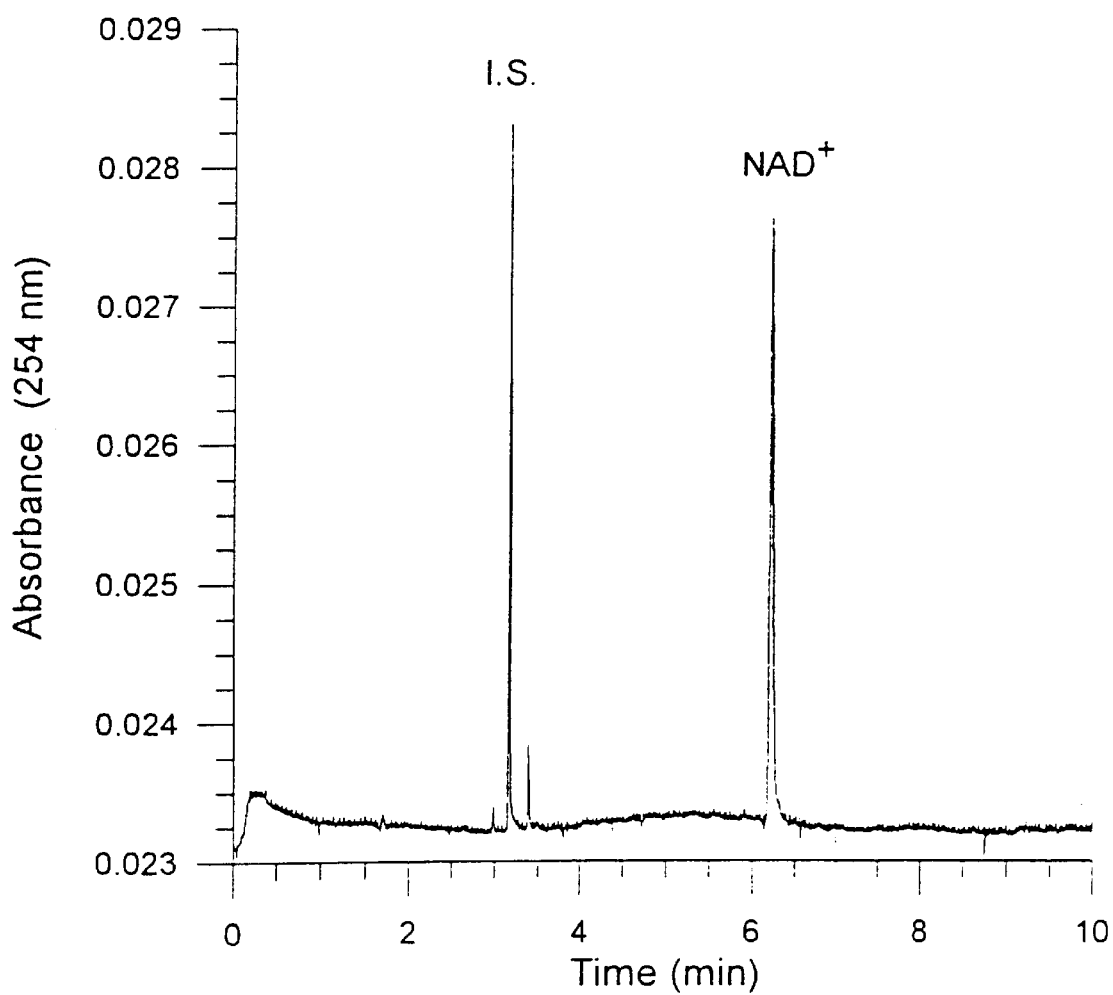

Under the same steady-state conditions outlined above, the $NAD^+$, produced during the enzymatic reaction, migrates through chamber 2 and is collected into chamber 1 (anodic reservoir). The conversion of NADH into $NAD^+$ has been followed by capillary zone electrophoresis. FIG. 5 gives an example of the separation and quantitation of $NAD^+$, monitored by sampling aliquots of the liquid. content of chamber 1. With the use of an internal standard and a calibration curve, it has been possible to estimate that 84% of the total NADH initially loaded into chamber 3 has been recovered in chamber 1 (the slight excess of unreacted NADH, once collected into chamber 1, would quickly be destroyed under these acidic conditions). The $NAD^+$ recovered in chamber 1, when neutralized at pH ca. 8.5, is still fully active as a coenzyme. It can thus be converted by alcohol dehydrogenase (using ethanol as substrate) back into NADH and then, if needed, pumped back into chamber 3 for sustaining enzyme reaction for extended periods of time.

Figure 6:
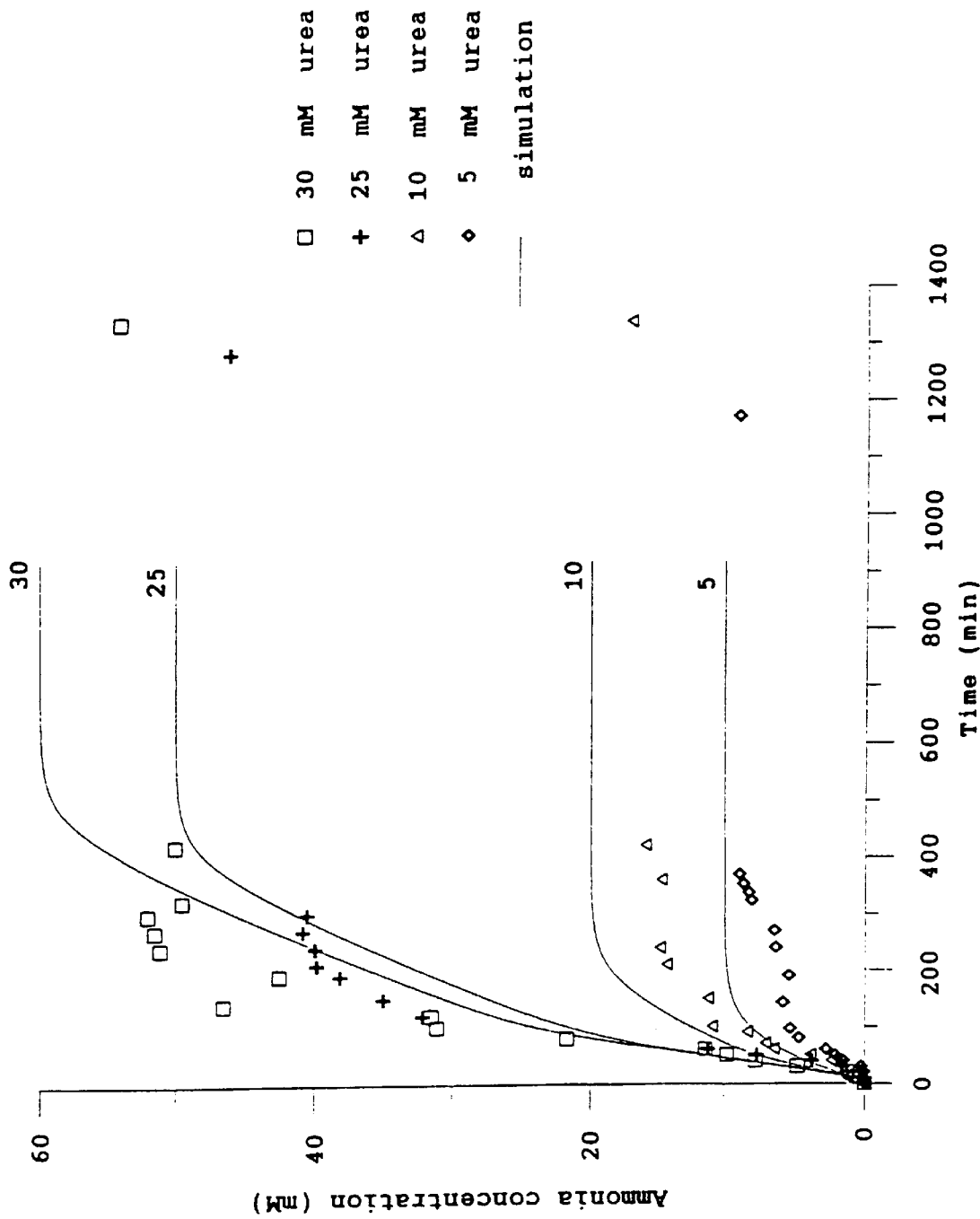
Figure 7:
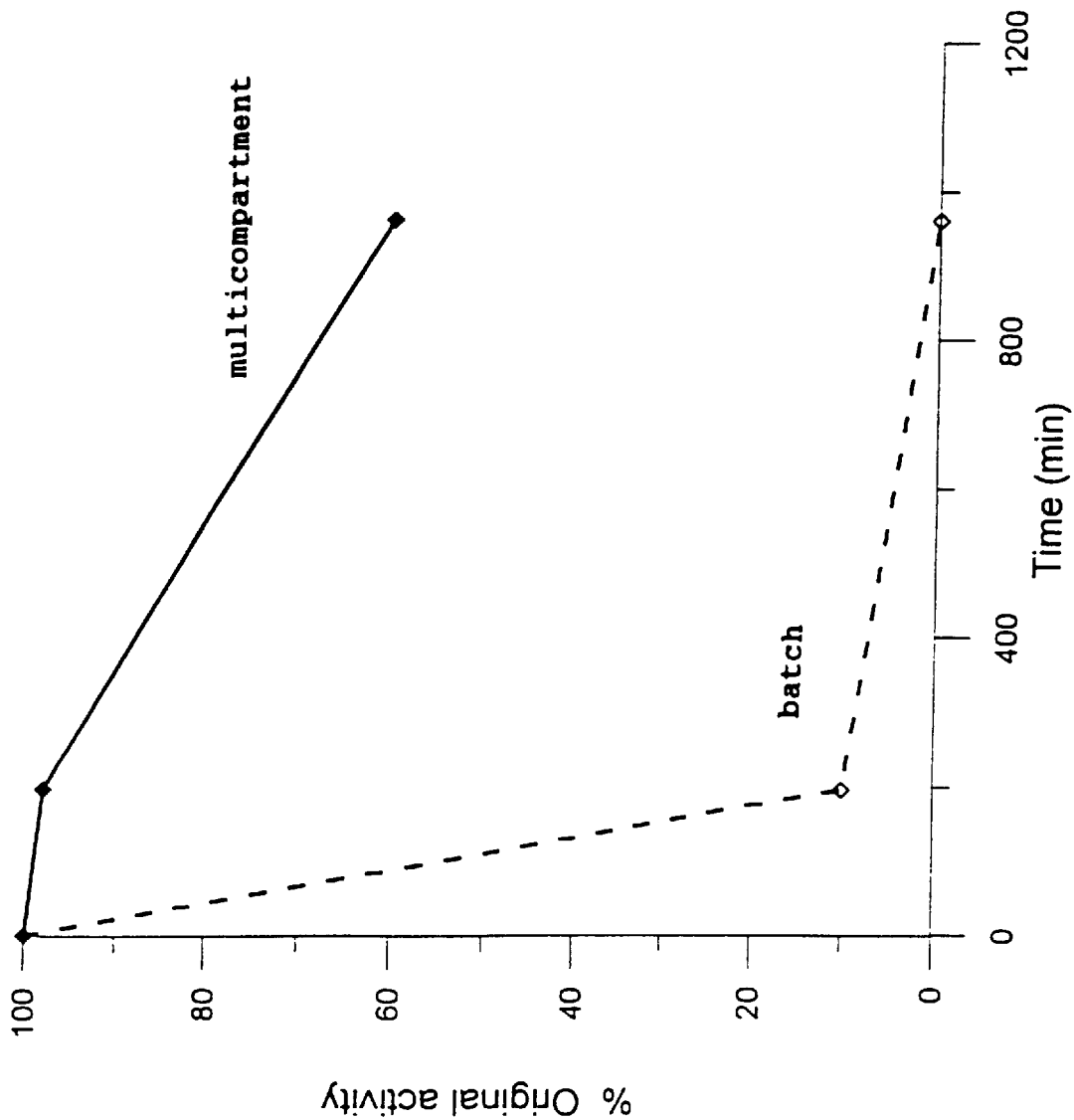

Another example of enzyme reaction in "isoelectric traps" is shown in FIG. 6, in the case of jack bean urease. Since the pH of optimum activity is 7.5 (but the pI is 4.9) both the enzyme and the buffer (50 mM histidine, pI 7.47) are trapped between two membranes having pI values of 4.5 (anodic) and 7.8 (cathodic). The reactor is assembled as in FIG. 2 (with 5 chambers), with the following membranes (from anode to cathode): pI 3.0, pI 4.5, pI 7.8 and pI 11. The anodic solution is dilute phosphoric acid (pH 2.5) and the cathodic solution is dilute NaOH (pH 11.5). The central chamber (with reservoir) (No. 3) contains a total of 50 mL of enzyme (70,000 units per gram solid; concentration: 4 mg/L) dissolved in 50 mM His. Produced ammonia is quantified according to Kerscher and Ziegerhorn (in: Methods of Enzymatic analysis, Bergmayer, H. U., Bergmayer, J. and Grassi, M., eds., 8, 1985, 444–453, VCH, Weinheim). The rate of ammonia production, in the electrolyzer, is measured for a wide interval of initial urea concentrations in the enzyme chamber (FIG. 6). Unlike batch reactions, where high initial rates are maintained for only 10 min, the multicompartment reactor allows sustained high reaction rates till plateauing due to substrate consumption. Continuous withdrawal of ammonia from the reaction chamber eliminates the product inhibition (the major reason of low reaction output in a batch). As a result, at all concentrations explored, the reaction yield is 92–95% in all cases, vs. 10 to 50% in a batch reactor. This high reaction yield should be coupled to maintenance of enzyme integrity during the reaction. In fact, as shown in FIG. 7, in a batch reactor the enzyme quickly looses its activity, only 10% of the initial activity remaining after 200 min. At the same time point, urease in the electrolyzer has lost only 2% of its catalytic activity.

The idea of immobilizing enzymes in between two isoelectric membranes, possessing high-enough buffering capacity so as to be impermeable to the trapped enzyme, is novel and offers unique advantages over the other types of reactors, consisting in true immobilization onto polymeric beads or into trapping against a ultrafiltration membrane. In the first case, insolubilized enzymes onto polymeric materials (in the form of beads, sheets, filaments) exhibit often much lower reaction rates and different $K_m$ and $K_i$ values, a drawback which does not occur in our "isoelectrically trapped" enzyme reactors, where such constants are the same as for a free, soluble enzyme. In the second case, one of the major drawbacks is that, upon activation of the ultrafiltration process, the flux can be severely hampered by the rapid formation of a concentration polarization layer of enzyme molecules or proteinaceous material building up against the membrane. In addition, the localized enzyme in the polarization layer cannot be utilized to its full reactivity because of the short contact time of the substrate with the enzyme. On the contrary, our multicompartment electrolyzer with enzymes trapped between two isoelectric membranes does not suffer from any of these drawbacks. The enzyme is not prevented from migrating by a sieving mechanism, but by a continuous titration process. There cannot be any build-up of enzyme molecules against the two isoelectric membranes. On the contrary, any enzyme molecule tangent to such membranes will be charged negatively (at the anodic side) or positively (at the cathodic side) and thus will be pulled away from the membrane by the electric field and forced to migrate towards the opposite pole. Conversely, any charged molecule (or zwitterion) not isoelectric within this pH range will be permeable to these two membranes and forced to migrate towards the electrode of opposite charge. Thus, the couple of membranes trapping any given enzyme acts like pH-stat units in our experimental set-up.

What is claimed is:

1. A process for enzyme immobilization, wherein:
   a) the enzymes are prevented from leaving an enzyme reactor chamber by using two buffering, isoelectric membranes, having pIs on either side of the enzyme pI;
   b) the migration of said enzymes is blocked by a continuous titration process.

2. A process according to claim 1, wherein the buffers present in the enzyme reaction chamber are amphoteric and exhibit pI values also comprised in between the pI values of the two isoelectric membranes trapping the enzyme.

3. A process according to claim 2, wherein the buffers have pI values comprised between pH 2 and 11, with an adequate buffer power at their pI values.

4. A process according to claim 1, wherein the reactor is operated in presence of enzyme-stabilizing agents.

5. A process according to claim 4, wherein the enzyme stabilizing agents bear a charge or are uncharged.

6. A process according to claim 4, wherein the enzyme stabilizing agents are selected from the group consisting of polyols, dextrans, polyethylene glycol, carbohydrates or their mixtures.

7. A process according to claim 1, wherein the enzyme reactor is coupled to an electric field, for transporting in and out of the enzyme cell substrates, cofactors and reaction products and any other ion needed for optimization of enzyme reactivity.

8. A process according claim 1, wherein the enzyme, while being trapped in the reaction chamber by isoelectric membranes, is not necessarily isoelectric, being buffered by the amphoteric buffer to the pH of optimum of activity, said pH differing from the enzyme pI, the difference of pI between the two membranes being however wide enough so as to maintain in the reaction chamber both the enzyme and the operative buffer.

9. An enzyme reactor comprising a reaction chamber in which the enzyme, while being kept in solution, is immobilized in between two buffering isoelectric membranes, having pI values on either side of the enzyme pI, said reactor being coupled to an electric field able to transport, in and out of the reaction chamber, substrates, cofactors, reaction products and any other ion suitable for the reaction, said electric field being coupled to a flux of liquid able to transport, via recycling, the enzyme to a reservoir acting as both, a heat sink for dissipating the joule heat and thermostating the enzyme at the desired reacting temperature and as a feeder for (charged or uncharged) substrates, cofactors, buffering ions and stabilizers, wherein said enzyme reactor is coupled to chromatographic columns and/or to other reaction chambers, adjacent to the reaction chamber or external to it.

10. A reactor according to claim 9, structured as a multicompartment reactor.

* * * * *